US010758742B2

(12) United States Patent
Shang

(10) Patent No.: US 10,758,742 B2
(45) Date of Patent: Sep. 1, 2020

(54) OPTICAL FIBER PUNCTURE NEEDLE TUBING AND USE THEREOF

(71) Applicant: Hua Shang, Jiangsu (CN)

(72) Inventor: Hua Shang, Jiangsu (CN)

(*) Notice: Subject to any disclaimer, the term of this patent is extended or adjusted under 35 U.S.C. 154(b) by 0 days.

(21) Appl. No.: 16/373,306

(22) Filed: Apr. 2, 2019

(65) Prior Publication Data

US 2020/0030623 A1    Jan. 30, 2020

Related U.S. Application Data

(63) Continuation of application No. PCT/CN2018/097461, filed on Jul. 27, 2018.

(51) Int. Cl.
  *A61N 5/00*   (2006.01)
  *A61N 5/06*   (2006.01)
  *A61B 17/34*  (2006.01)

(52) U.S. Cl.
  CPC .......... *A61N 5/0601* (2013.01); *A61N 5/062* (2013.01); *A61B 17/3421* (2013.01); *A61B 2017/3454* (2013.01); *A61N 2005/063* (2013.01); *A61N 2005/0612* (2013.01)

(58) Field of Classification Search
  CPC .................. A61N 5/0601; A61N 5/062; A61N 2005/0612; A61B 2017/320733; A61B 2017/320741; A61B 17/32053; A61B 17/3207; A61B 2017/3433; A61B 2017/3454; A61B 2017/348
  See application file for complete search history.

(56) References Cited

U.S. PATENT DOCUMENTS

| 2007/0093780 | A1* | 4/2007 | Kugler | A61B 17/221 604/510 |
| 2007/0233221 | A1* | 10/2007 | Raju | A61F 2/82 623/1.11 |
| 2009/0304576 | A1* | 12/2009 | Warren | A61K 9/0024 424/1.11 |
| 2015/0012072 | A1* | 1/2015 | Johnson | A61N 5/0601 607/92 |
| 2018/0317949 | A1* | 11/2018 | Lenker | A61M 25/09025 |
| 2019/0099195 | A1* | 4/2019 | Carroll | A61B 17/32002 |
| 2019/0160306 | A1* | 5/2019 | Rabiner | A61M 25/10 |

FOREIGN PATENT DOCUMENTS

JP        2000354626 A   * 12/2000

* cited by examiner

*Primary Examiner* — Michael W Kahelin
*Assistant Examiner* — Sana Sahand
(74) *Attorney, Agent, or Firm* — Hauptman Ham, LLP

(57) ABSTRACT

An optical fiber puncture needle tubing comprises an optical fiber having a body portion and a head portion, one end of the tapered head is a tapered tail end having a tapered diameter; the periphery of the body portion is wrapped with a body tube, the cylindrical head is wrapped with a metal casing, and the periphery of the tapered head is wrapped with a polymer jacket. The polymer jacket is provided with an inverted-tooth structure or inverted kerf structure. Through the synergistic effect with various components, the puncture needle tubing can be transmitted fast in the long blood vessels, and can achieve higher light emission efficiency and therapeutic effect. The puncture needle tubing can be applied in fields of the treatment of photodynamic tumors, eliminating vascular obstructions or performing vascular puncture.

10 Claims, 5 Drawing Sheets

OPTICAL FIBER PUNCTURE NEEDLE TUBING AND USE THEREOF

PRIORITY CLAIM

The present application is a continuing application of PCT Patent Application No. PCT/CN2018/097461, filed Jul. 27, 2018, which is incorporated herein by reference in its entirety.

TECHNICAL FIELD

The present disclosure relates to the technical field of medical instruments, in particular to an optical fiber puncture needle tubing and a use thereof.

BACKGROUND

Photodynamic Therapy (PDT) is a new technology for the diagnosis and treatment of diseases by using the photodynamic effect. This therapy is based on the photodynamic effect. This is a photosensitization reaction with biological effects in which oxygen molecule is involved. It comprises the following processes: the photosensitizer absorbed by a tissue is excited by the irradiation of a specific wavelength of laser; and then the excited state of the photosensitizer transfers energy to the oxygen in the surrounding environment, to generate a highly active singlet oxygen; singlet oxygen and adjacent biomacromolecules occur oxidation reaction, and thus produce cytotoxicity, which in turn leads to cell damage and even death. Compared with traditional therapies, photodynamic therapy has the advantages of less trauma, good targeting, no drug resistance and side effects. However, since photodynamic therapy mainly uses in the range of more than 600 nm wavelength in the red light region, the light in this region will be lost due to the absorption in a human body. Generally, only the light having the wavelength in few millimeters to several tens of millimeters can be transmitted. For some tumors deep in the body, photodynamic therapy is ineffective. With the aid of optical fiber, endoscopes, and other interventional techniques, the laser can be directed into the deep of body for treatment, avoiding the trauma and pain of surgery such as thoracotomy and laparotomy. Currently, light can be introduced into the body by a puncture needle comprising optical fiber, but since light needs to be led out of fiber optics, it is necessary for the tip of needle to have a hole with a sufficient size to allow light to pass out, increasing the diameter of the needle. In order to overcome the resistance during puncturing, the optical fiber is wrapped by a hard metal material. Therefore, the needle tubing is thicker. During the process for puncturing, a large pressure is required to perform the puncturing, which is likely to cause a larger trauma and damage to the normal vascular tissue, and bleeding. Therefore, for this series of problems, the present disclosure has developed an optical fiber puncture needle tubing.

SUMMARY

In view of the above, an object of the present disclosure is to provide an optical fiber puncture needle tubing and the use thereof, so as to solve defects in the prior art.

The object of the present disclosure can be achieved by the following technical solutions.

An optical fiber puncture needle tubing is provided. The puncture needle tubing comprises an optical fiber comprising a body portion and a head portion, in which the head portion comprises a cylindrical head and a tapered head, the forefront end or the free end of the tapered head is a tapered tail end having a tapered diameter formed by a taper method; the periphery of the body portion is wrapped with a body tube, the cylindrical head is wrapped with a metal casing, and the periphery of the tapered head is wrapped with a polymer jacket; one end of the metal casing is fixedly connected with the body tube, and the other end is fixedly connected with the polymer jacket; in the polymer jacket, the part thereof corresponding to the tapered tail end is a taper structure having a tapered diameter; in which an inverted-tooth structure or inverted kerf structure is provided on the outside of the polymer jacket, so as to have a smaller resistance when advancing, and have a larger resistance when retreating, thereby effectively reducing the thrust required for puncturing.

Further, the metal casing is tightly wrapped around the periphery of the cylindrical head of the optical fiber, to integrally connect the optical fiber with the metal casing; the metal casing has a spiral structure with spiral kerfs formed on a metal tube by laser cutting, so that it has a certain strength while increasing a certain flexibility.

Further, the body tube is a spiral tube comprising a plurality of spiral coils, and the spiral tube has a spiral structure with spiral kerfs formed by laser cutting.

Further, the outside of the body portion of the optical fiber is coated with a body portion cladding layer for preventing the light from being emitted from the side surface of the optical fiber; the refractive indexes of the tapered head of the optical fiber and the polymer jacket are 1.45 to 1.55.

Further, the tapered head 2 has 7° to 25° of taper angle β.

Further, the inverted-tooth structure outside the polymer jacket is formed by a plurality of frustule structures with a small front-end diameter and a large rear-end diameter, so as to make the fiber puncture needle tubing easier to move forward and not easy to retreat.

Further, the inverted kerf structure outside the polymer jacket are formed on the outer surface of the metal tube in the shape of wedge by laser cutting, the inverted kerfs are inclined backward, and the width of the inverted kerfs decreases gradually from the outside to the inside end.

Further, in the inverted-tooth structure, the thickness of the front end of the frustule structure is 50 to 70 μm, and the thickness of the rear end of the frustule structure is 90 to 110 μm, and the difference in the thickness between the front end and the rear end is 30 to 50 μm.

Further, an end of the optical fiber puncture needle left outside the body is connected with a drive device capable of vibrating backwards and forwards, in order to apply a forward force to the optic fiber puncture needle while vibrating.

Further, the drive device is a sonic vibration motor, has 10 μm to 500 μm of amplitude of vibration backwards and forwards, and 10 Hz to 1000 Hz of a vibration frequency.

Further, the cylindrical head of the optical fiber at the kerfs of the spiral casing does not provide with a cladding layer, or has a cladding layer with the refractive index slightly smaller than that of the cylindrical head of the optical fiber, so that a part of the light can be emitted from the kerfs of the spiral casing.

Further, the length of the head portion is 7 to 10 mm, and the length of the polymer jacket is 2.5 to 4 mm; the length of the metal casing is 4.5 to 6 mm.

Further, in the metal casing, the width of the kerf is 0.1 to 0.2 mm, the width of the metal sheet for making the spiral structure of the metal casing is 0.2 to 1 mm.

Further, the thickness of the body tube is 0.05 to 0.1 mm, the width a of the kerfs for forming the spiral structure is 0.02 to 0.2 mm, the width of the spiral sheet for making the spiral structure is 0.5 to 3 mm.

Further, in the tapered head, the diameter at the foremost end of the tapered head is 10 to 50 μm.

Further, the length of the body tube is 1 to 2 m; the body tube is made by a biomedical metal material including but not limited to one of stainless steel, synthetic fiber, carbon fiber, titanium alloy, gold, silver.

The present disclosure also provides a use of the optical fiber puncture needle tubing, in which the optical fiber puncture needle tubing is used in the movement in the long blood vessels, in the puncturing of blood vessel wall, in the photodynamic oncology and the irradiation of blood vessels, tissues or organs deep in human body.

The present disclosure provides an optical fiber puncture needle tubing and the use thereof, the beneficial effects thereof is mainly in that: through the synergistic effect with various components, the puncture needle tubing can be transmitted fast in the long blood vessels, such as being able to smoothly pass through blood vessels up to 2 m long, and can achieve higher light emission efficiency and therapeutic effect, so that it has important application value and significance in the treatment of photodynamic tumors. In addition, the puncture needle tubing also can be applied in other fields, such as eliminating vascular obstructions or performing vascular puncture, etc.

The present disclosure subtly adopts a tapered head with a thinner diameter formed by the taper method which is used as the head portion of the optical fiber, the effective irradiation rate of light is greatly improved, which is beneficial to the effective cooperation of light and photosensitizer, and reduces the waste of light or photosensitizer, thereby increasing the treatment effect and reducing costs. More importantly, by controlling the specifications of the tapered head, refractive index, the angle of the tapered head or the tapered tail, as well as the refractive index of polymer jacket, the present disclosure achieves that the light emitted from the tapered head can mainly irradiate to a certain angle in the front. Therefore, the present disclosure can significantly increase the irradiation efficiency and the treatment effect, thereby reducing the waste rate of the light and photosensitized and increasing the efficiency thereof.

The cylindrical head auxiliary irradiates epitaxial components. The spiral metal casing which is wrapped around the cylindrical head plays an important ropy in the flexibility and strength of the head portion in the puncture needle tubing. More importantly, the length, the spiral kerf, and the width of spiral sheet or metal sheet have extremely important auxiliary therapy on the photodynamic tumor treatment. That is, a small amount of light can be emitted from the kerfs of the metal casing when the light is emitted from the tapered head, so as to help the tapered head to realize the effective treatment of the whole tumor.

The tapered head is finer, which makes it more flexible, less brittleness and less likely to break. The inverted-tooth structure or the inverted kerf structure on the polymer jacket makes the forward resistance smaller and the backward resistance larger, which effectively reduces the thrust required for puncturing, makes the movement of the puncture needle tubing smoother in the blood vessels, and reduces the difficulty and time of surgery. More importantly, the polymer jacket can further protect the optical fiber, making the tapered head not easy to break. Even if the tapered head is broken, the polymer jacket will still protect the tapered head, so that it will neither damage the blood vessels, nor be lost in the body.

The present disclosure is designed with an inverted-tooth structure or inverted kerf structure outside the polymer jacket, and is equipped with a vibration motor, so as to realize an effective transmission which is convenient to advance and not easy to retreat, and is favorable for moving smoothly in the blood vessels.

The puncture needle can regularly undergo a slight deformation under the design of the vibration motor. Moreover, the pitch of the spiral part is decreased, thereby helping to move forward in the blood vessels. Meanwhile, the polymer jacket prevents it from retreating and thus increases the transmission effect greatly.

In summary, the present disclosure has good clinical application effect, strong practicability, and a potential value for promotion and application.

Figure 1:
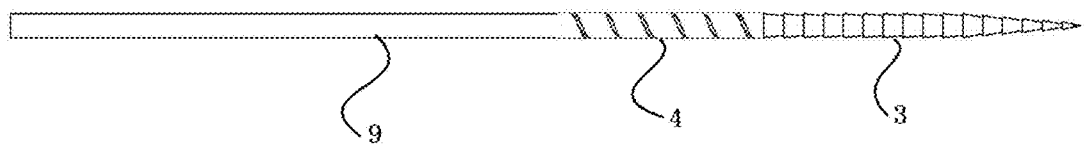
FIG. 1 is a schematic structure diagram of the whole optical fiber puncture needle tubing according to Example of the present disclosure.

LIST OF REFERENCE SYMBOLS 1 cylindrical head
2 tapered head
3 polymer jacket
4 metal casing
8 body portion
9 body tube 21 tapered tail end
31 taper structure
32 inverted-tooth structure
33 inverted-kerf
106 body tube casing
107 hydrophilic coating

DETAILED DESCRIPTION

Various examples of the present disclosure are described below for details. Apparently, the described examples are only a part of examples in the present disclosure, rather than all of them. While the following contains many specific implementation details, they should not be construed as limitations on the scope of any claims, but rather as descriptions to particular examples. Based on the examples provided by the disclosure, other examples obtained by those skilled in the art without creative efforts are encompassed in the scope of the disclosure.

Example 1

As shown in FIGS. 1-4, an optical fiber puncture needle tubing comprising an optical fiber is provided. The optical fiber comprises a body portion 8 and a head portion. The head portion comprises a cylindrical head 1 and a tapered head 2. The forefront end and the free end of the tapered head 2 is a tapered tail end 21 having a tapered diameter formed by a taper method. One end of the cylindrical head 1 is fixedly or integrally connected to the body portion 8 or integrally shaped with the body portion 8, the other end is fixedly or integrally connected with the end having a larger diameter of the tapered head, or they are integrally shaped.

Figure 2:
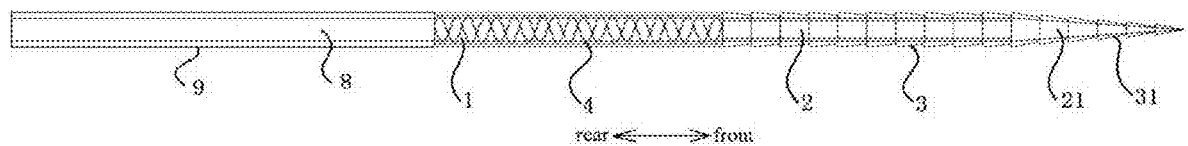
FIG. 2 is a perspective structure diagram of the optical fiber puncture needle tubing according to Example of the present disclosure.

The periphery of the body portion 8 is wrapped with a body tube 9, and the cylindrical head 1 is wrapped with a metal casing 4. The metal casing 4 wraps around the periphery of the cylindrical head 1 tightly, to integrate the cylindrical head 1 of the optical fiber with the metal casing 4. The periphery of tapered head 2 is wrapped with a polymer jacket 3. One end of the metal casing 4 is fixedly connected with the polymer jacket, and the other end of the metal casing is fixedly or integrally connected with the body tube. As shown in FIG. 1-2. The head portion of optical fiber and the metal casing 4 outside the head portion and the polymer jacket 3 can be collectively referred to as a head end.

Figure 3:
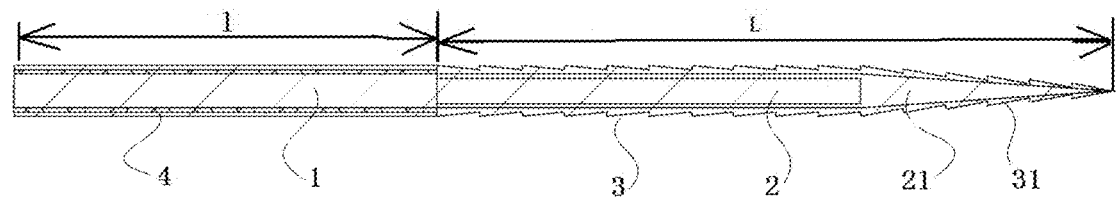
FIG. 3 is a cross-sectional diagram of the head portion end according to Example of the present disclosure.
Figure 4:
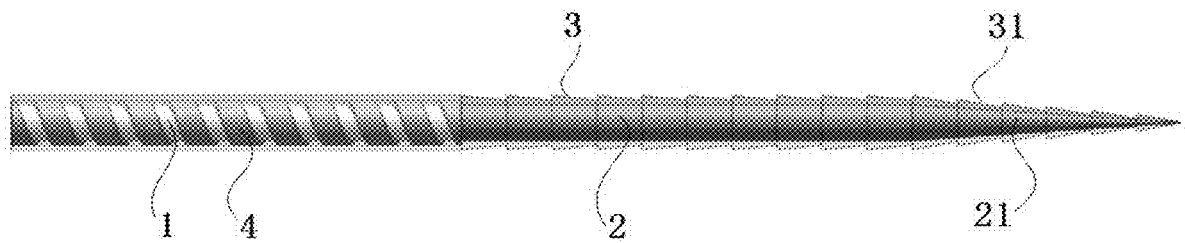
FIG. 4 is a perspective structure diagram of the head portion end according to Example of the present disclosure.

The polymer jacket 3 is transparent. In the polymer jacket 3, the outer side corresponding to the tapered tail end 21 of the optical fiber is provided with a structure 31 having the tapered diameter, which is consistent with the tapered tail 21 of the tapered head 2 in the structure, as shown in FIGS. 2-4.

The polymer jacket 3 may be formed by polyamide or polypropylene. The polymer jacket 3 is provided with an inverted-tooth structure or an inverted kerf structure, as shown in FIGS. 1-4. Such structure has a small resistance when advancing, and has a larger resistance when retreating, so that it can puncture in a progressive manner under the applied sight impact, and can effectively reduce the force required for puncturing.

As a further preferred embodiment, the inverted-tooth structure 32 of the polymer jacket 3 is formed by a plurality of frustule structures with a small front-end diameter and a large rear-end diameter, i.e., the plurality of frustule structure are arranged on the periphery of the tapered head by end to end, so as to make the fiber puncture needle tubing easier to move forward and not easy to retreat.

Figure 5:
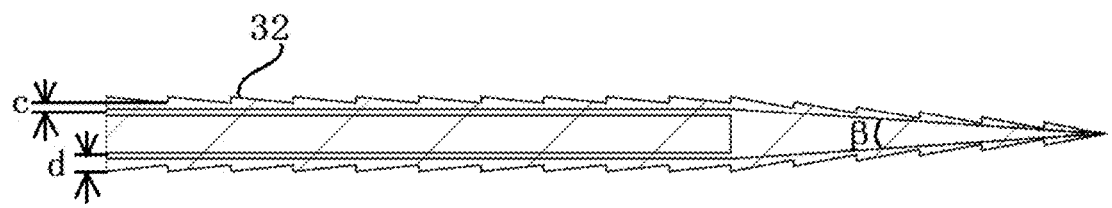
FIG. 5 is a schematic diagram illustrating the thickness of the polymer jacket according to Example of the present disclosure.

Specifically, as shown in FIG. 5, in the inverted-tooth structure 32, the thickness c of the front end of the frustule structure is 50 to 70 μm, and the thickness d of the rear end of the frustule structure is 90 to 110 μm, and the difference in the thickness between the front end and the rear end is 30 to 50 μm. Controlling thickness is quite important for effective and smooth transmission and advancement. If the thickness difference is too large, it either needs to increase the outer diameter of the metal casing, or needs to reduce the inner diameter of the metal casing, which has a greater influence on the overall puncture needle tubing. In addition, if the thickness difference is too large, the thickness of the back side of the frustule will be increased greatly, which in turn increases the resistance during advancing. Moreover, for the small or fine blood vessels, it will increase the degree of damage to the inner wall of the blood vessels. If the thickness difference is too small, it will not play the role of assisting advancement and preventing retreating. Therefore, the thickness of the inverted-tooth structure 32 and the difference in thickness between the front end and the rear end of the frustule have important influence on the advance of the optical fiber puncture needle tubing.

As a further preferred embodiment, as shown in FIGS. 2-4, the metal casing 4 is a spiral metal casing. The metal casing 4 has a spiral structure with spiral kerfs formed on a metal tube by laser cutting, so that it has a certain strength while increasing a certain flexibility.

Figure 6:
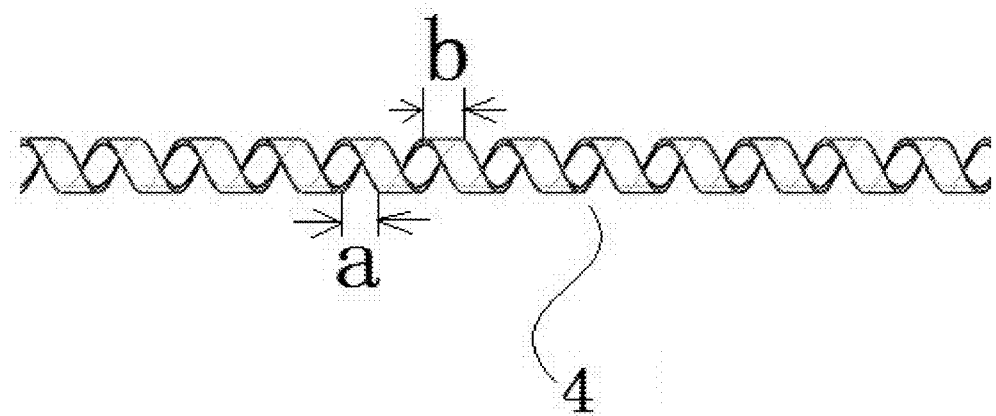
FIG. 6 is a schematic structure diagram of the metal casing according to Example of the present disclosure.

More preferably, in the metal casing 4, as shown in FIG. 6, the width a of the kerf is 0.1 to 0.5 mm, such as 0.1 mm, 0.2 mm, 0.3 mm, 0.4 mm, 0.5 mm etc., and the width b of the metal sheet for making the spiral structure of the metal casing 4 is 0.2 to 1 mm, such as 0.2 mm, 0.4 mm, 0.6 mm, 0.8 mm, 1 mm, etc. The values of the kerf width a and the spiral sheet width b, as well as the cooperation thereof directly affect the ability to pass through the blood vessels and the smoothness of passing through the blood vessels, and also affect the puncture strength from one blood vessel to another. Width a and width b that are too wider and too narrow will affect its flexibility and strength. If the strength is too high, it cannot pass through the curvature of the blood vessel, and the damage to the inner wall of the blood vessel will be serious; if the flexibility is too high, it cannot pass through the blood vessel having a longer length, especially, when the length of blood vessels to be passed through is within 1 m, it may pass through blood vessels relatively easier, while when the length beyond 1 m, it will be difficult for the structure to pass through such blood vessels. In addition, it is not easy for the user to control the strength and direction through the handheld end. Moreover, when piercing and entering another blood vessel from one blood vessel, a lower strength will lead to the inability to pierce the blood vessel. Therefore, when the strength is too high or the flexibility is too high, the device cannot reach blood vessels or organs buried inside the body in a certain depth, such as liver tumors. A good effect can only be achieved upon the suitable width a and suitable width b.

As a further preferred embodiment, an end of the optical fiber puncture needle tubing left outside the body is connected with a drive device capable of vibrating backwards and forwards, in order to apply a forward force to the optic fiber puncture needle tubing while vibrating.

Preferably, the drive device is a sonic vibration motor, i.e., vibration motor has 10 μm to 500 μm of amplitude of vibration backwards and forwards, and 10 Hz to 1000 Hz of a vibration frequency.

Figure 7:
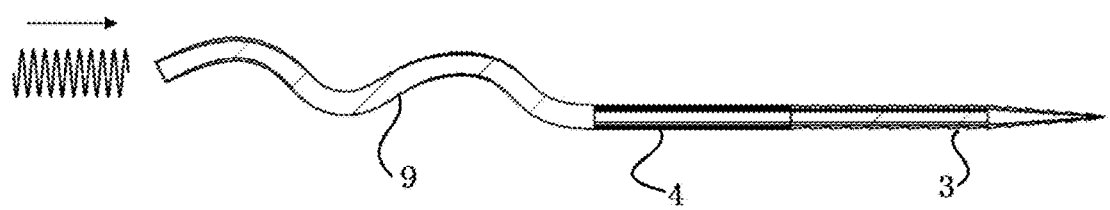
FIG. 7 is a schematic diagram illustrating the structure during the movement of the optical fiber puncture needle tubing according to Example of the present disclosure under the drive of the vibration motor.
Figure 8:
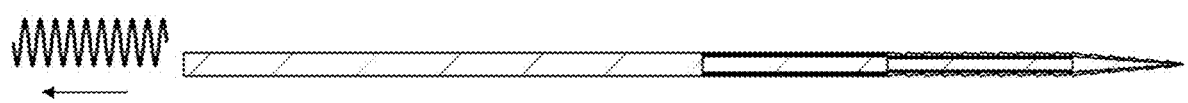
FIG. 8 is a schematic diagram illustrating another structure during the movement of the optical fiber puncture needle tubing according to Example of the present disclosure under the drive of the vibration motor.

For example, when puncturing, the puncture needle tubing is connected with the sonic vibration motor which has 100 Hz of the vibration frequency and 50 μm of the vibration amplitude. As shown in FIGS. 7-8, when the sonic vibration motor vibrates forward, the whole structure of the puncture needle tubing is deformed to conduct the vibration. As shown in FIG. 7, the puncture needle is slightly deformed when vibrating forward. The deformation includes the bending of the puncture needle tubing and the shrinkage in the pitch of the metal casing 4. Such elastic deformation causes the tip of the needle to move forward and overcome the resistance, so as to achieve the forward puncture. When vibrating backward, as shown in FIG. 8, since the polymer jacket 3 has the inverted-tooth structure, the friction is much greater than the forward movement, the puncture needle tubing is pulled and moved forward as whole, but the tip of the needle may stay still. The puncture needle tubing continues to puncture forward under the effect of multiple vibrations while applying additional force. This means of puncturing requires less force than the conventional puncture needle, thus allowing the optical fiber puncture needle to be finer and softer, and at the same time capable of completing the puncture effect.

As a further preferred embodiment, the length of the head portion is 7 to 10 mm, in which the length L of the polymer jacket 3 is 2.5 to 4 mm, such as 3 mm. The length 1 of the metal casing 4 or the cylindrical head 1 is 4.5 to 6 mm, such as 5 mm; as shown in FIG. 3. If the length of polymer jacket 3 or tapered head 2 is too long, it will be easy to cause damage to blood vessels, and will be difficult to move at the slight bend of blood vessels. If too short, the puncturing effect will not be achieved. In addition, it is impossible to move smoothly and fast in blood vessels with the cooperation of vibration motor. If the metal casing 4 is too long or too short, it is neither helpful for moving in blood vessels, or can achieve good auxiliary effect on the puncturing blood vessel walls by tapered head 2. More importantly, the spiral kerfs of the metal casing 4 may emit out a certain light, so as to achieve the auxiliary therapy. Therefore, the widths of kerf and the metal sheet, as well as the length of the metal casing 4 play an important role in the therapeutic effect. Therefore, only when the length is suitable, it can pass through the blood vessels smoothly and achieve good transmission, puncturing, thereby having a synergistic effect on the puncture needle tubing.

As a further preferred embodiment, the length of the body tube 9 is 1 to 2 m, such as 1.8 m. The length of the body tube 9 is the same as that of the body portion 8 of the optical fiber. The body tube is tightly wrapped around the body portion 8 of the optical fiber, so that they can be integrated together for easy transmission.

The body portion 8 and the cylindrical head 1 of the optical fiber may have a diameter of 400 μm, which may be a quartz fiber. In the tapered head, the diameter at the foremost end of the tapered tail end is 10 to 50 μm, such as 20 μm, 30 μm, 40 μm. Such fineness can increase the flexibility and reduce the brittleness thereof. The metal casing 4 and the body tube 9 may have an outer diameter of 600 μm and an inner diameter of 400 μm.

In this example, when using, the end of the head portion of the puncture needle tubing first pierces into the blood vessel and then transmits in the blood vessel, and the end of the puncture needle tubing left outside of the body can be connected with the vibration motor, so as to assist the puncture needle reaching a predetermined site, such as a tumor in the body (e.g., liver tumors) via the blood vessel. Then, the optical fiber puncture needle tubing is connected with a laser, and the laser is turned on, so as to transmit the light to the body tube of the optical fiber, and then transmit to the tapered head, and finally via the polymer jacket irradiate to the tumor which has been applied the photosensitizer.

Example 2

On the basis of example 1, the body tube 9 is a spiral tube containing a plurality of spiral coils, and the spiral tube has a spiral structure with spiral kerfs formed by laser cutting.

Figure 9:
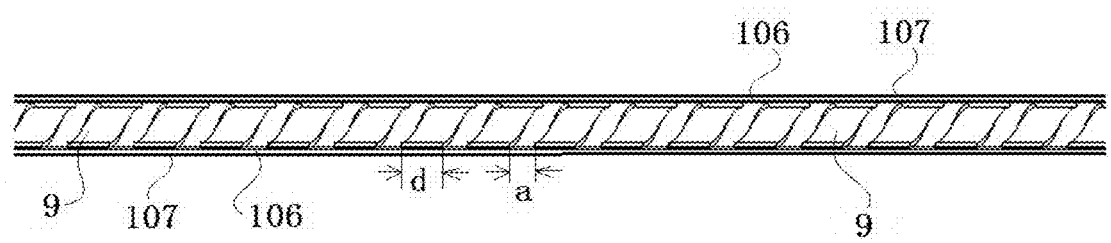
FIG. 9 is a section diagram of the structure of the body tube according to Example of the present disclosure (viewing from the center to the outside)

As shown in FIG. 9, it shows a cross-section of the body tube 9, viewing from center to the outside. In the body tube 9, the width a of the kerf is 0.02 to 0.2 mm, such as 0.05 mm, 0.08 mm, 0.1 mm. 0.15 mm, etc., the width d of the spiral sheet for making the spiral structure in the body tube 9 is 0.5 to 3 mm, such as 1 mm, and the thickness thereof is 0.05 to 0.1 mm, such as 0.08 mm. The length of the body tube 9 is nearly 2 m, and usually 1 to 1.8 m thereof will enter the human body. In addition, the human blood vessels have different thicknesses and a certain degree of curvature. As the blood vessels to be passed through are so long, and the environment are so specific, there are highly requirement for its strength and flexibility. The values of the kerf width a and the spiral sheet width d, as well as the cooperation thereof directly affect the ability to pass through the blood vessels and the smoothness of passing through the blood vessels, and even affect the strength of the head portion puncturing the tumor blood vessel walls. The width a and width d that are too wider or too narrow will affect the flexibility and strength. A good effect can only be achieved upon the suitable width a and suitable width d.

The body tube 9 is made of a biomedical metal material including but not limited to one of stainless steel, synthetic fiber, carbon fiber, titanium alloy, gold, silver, etc., preferably stainless steel. As a whole, the body tube is composed of one winding wire (may be two or more winding wires) wrapped around the periphery of body portion 8 of the optical fiber and made of the stainless steel actually.

Figure 10:
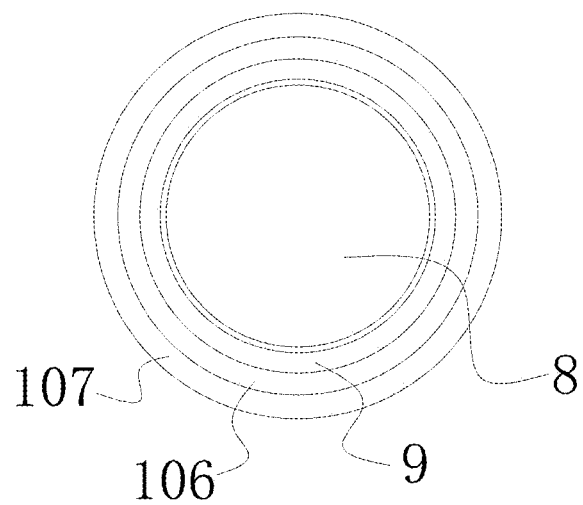
FIG. 10 is a cross-sectional diagram illustrating the body tube wrapped outside the body portion of the optical fiber according to Example of the present disclosure.

As shown in FIGS. 9-10, a body tube casing 106 is provided outside of the body tube 9, to increase the sealing of the guide tube and reduce the resistance; the material of the body tube casing 106 may be polyamide or polypropylene, etc., and other polymers may be acceptable. A hydrophilic coating 107 is provided outside of the body tube casing 106, to increase blood compatibility. The hydrophilic coating 107 is made of a chemically stable material including but not limited to, polytetrafluoroethylene, silicone rubber, polyethylene, polyvinyl chloride, fluorocarbon polymers, and polyurethane. The hydrophilic coating is applied to reduce the resistance in the blood vessel and to pass through the long blood vessels with complex internal environment.

The hydrophilic coating 107 in this example may be replaced with a hydrophobic coating.

Example 3

Figure 11:
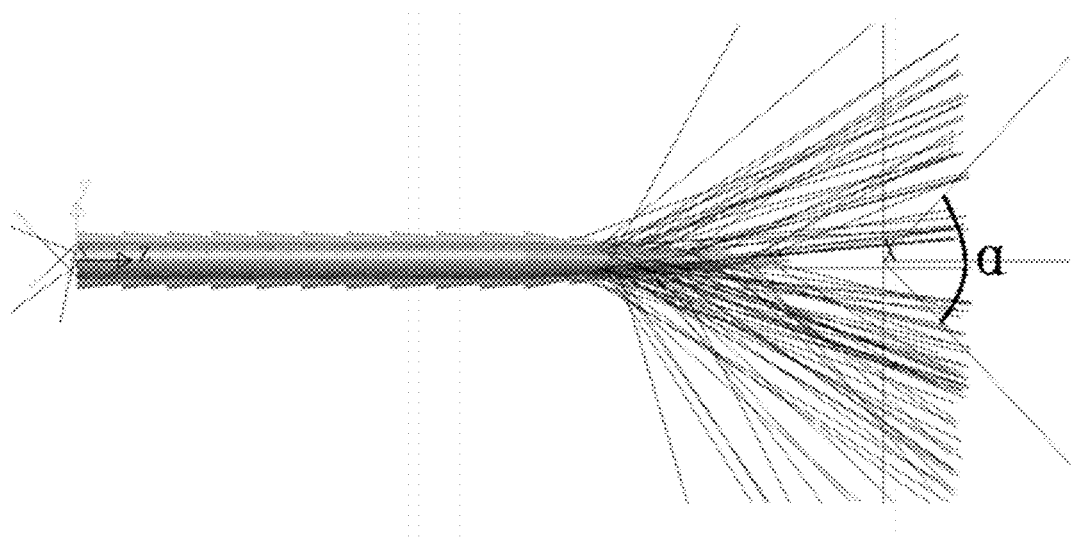
FIG. 11 shows the emission range of light on the tapered head or the polymer jacket according to Example 3 of the present disclosure.

On the basis of example 2, the refractive index of the tapered head 2 of the optical fiber is 1.45 to 1.55, preferably 1.5; while the refractive index of the polymer jacket 3 is 1.45 to 1.55, such as 1.45, 1.5, 1.55. And the taper angle $\beta$ of the tapered tail end 21 in the tapered head 2 is 7 to 25°, as shown in FIG. 5. The taper angle in the taper structure of the polymer jacket 3 is substantially consistent with that of the tapered tail end 21, which can substantially ensures that the light from the tapered head is in the range of 60 to 120°, the angle of which is indicated by a in FIG. 11. Specifically, through an optical simulation, it can be known that if the taper angle β is 22°, then the divergence angle α of the light is within 120°; and if the taper angle β is 7.6°, the divergence angle α of the light is within 60°. Therefore, when the taper angle β of the taper head 2 is 7 to 25°, the light on the tapered head can be efficiently directed to the target position, such as a tumor containing a photosensitizer, so as to effectively utilize the light energy and greatly increase the light output rate.

The refractive index of the entire optical fiber may be 1.5. However, it is preferable that the outer surface of the body portion 8 of the optical fiber is coated with a cladding layer having a refractive index, such as 1.2, 1.3, etc., lower than that of the optical fiber, so that the light does not exit from the body portion 8 of the optical fiber, restricting the light. Therefore, light can only be emitted from the tapered head. Thus, the light can directly irradiate onto the tumor containing the photosensitizer via the polymer jacket.

Preferably, the optical fiber at the spiral metal casing 4, i.e., the cylindrical head 1 of the optical fiber at the kerfs of the spiral casing does not provide with a cladding layer or has a cladding layer with the refractive index slightly smaller than that of the cylindrical head 1 of the optical fiber. Then, a part of the light can be emitted from the kerfs of the spiral casing, so as to irradiate the other auxiliary parts. Therefore, the key part can be directly irradiated by the tapered head for effective irradiation, and meanwhile the cylindrical head 1 assists the irradiation of the epitaxial part, thereby realizing effective irradiation of the whole part to be irradiated. Irradiation of tumor tissue containing a photosensitizer can effectively increase the efficacy of the photosensitizer and ultimately increase its therapeutic effect.

Figure 12:
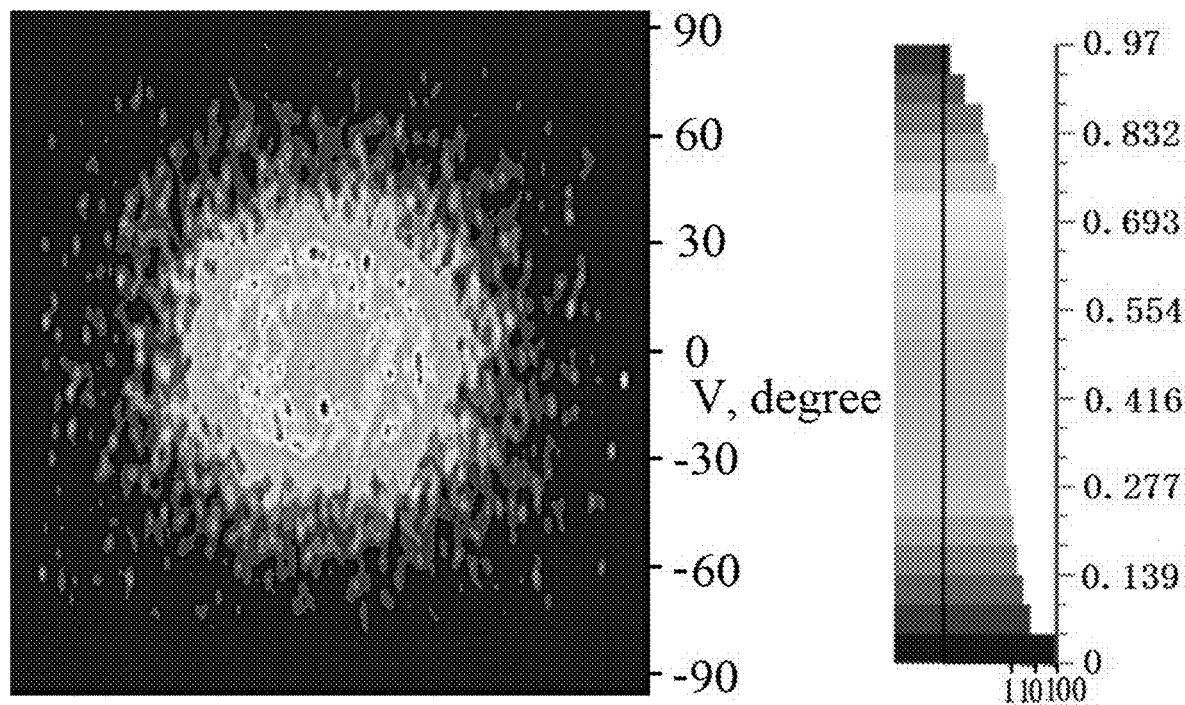
FIG. 12 shows the exit spot of the tapered head according to Example of the present disclosure.

In this example, if the input optical fiber has a wavelength of 650 nm, when the input power is 1 W, the output rate of the light output from the optical fiber tapered head is 0.94 W, the output power is high. In addition, the divergence angle thereof is about 60°, which can effectively irradiate or treat the key parts. The shape of the spot is shown in FIG. 12.

Example 4

Figure 13:
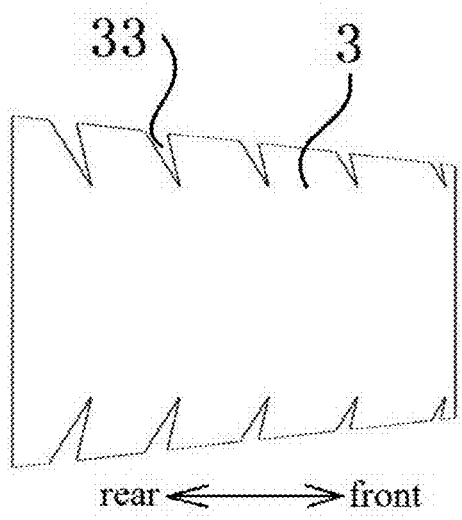
FIG. 13 shows the structure of the out surface of the metal casing according to Example 4 of the present disclosure.
Figure 14:
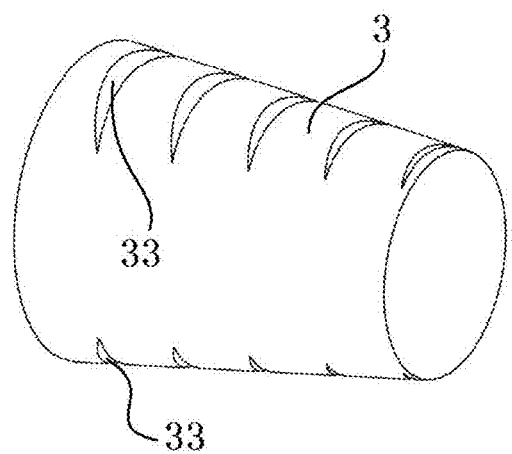
FIG. 14 shows the structure of the out surface of the metal casing according to Example 4 of the present disclosure.

On the basis of any of the examples 1-3, the polymer jacket 3 may have a structure that the outer surface thereof is designed with a plurality of inverted kerfs 33, as shown in FIGS. 13-14. That is, the inverted kerfs 33 is formed on the outer surface on the metal tube in the shape of wedge by laser cutting, and the inverted kerfs 33 are inclined backward, as shown in FIG. 13. The width of the inverted kerfs 33 decreases gradually from the outside to the inside end, and the thickness thereof also decreases gradually.

Preferably, the polymer jacket 3 in this example may have a structure with tapered diameter from the rear to the front end, which is convenient for advancing, as shown in FIGS. 13-14.

The inverted kerf structure makes the forward resistance smaller and the backward resistance larger, which effectively reduces the thrust required for puncturing, makes the movement of the puncture needle tubing smoother in the blood vessels, and reduces the difficulty and time of surgery.

Example 5

The present discloses relates to the use of the optical fiber puncture needle tubing. The puncture needle tubing can be used in the smooth movement in the long blood vessels, the effective puncture of blood vessel wall or intravascular obstruction, and the irradiation of the blood vessels, tissue or organ deep in human body. Therefore, such puncturing needle tubing can be effectively used in dredge of obstructions in blood vessels and in the dredge or treatment of congestion or clots in tissues.

If the optical fiber puncture needle tubing is used in photodynamic tumor treatment and the interventional treatment is used for a liver tumor, the optical fiber puncture needle tubing pierces into the liver artery through the femoral artery, and finally enters the blood vessel of the liver tumor. Then, the laser is turned on. Therefore, the light reaches the tapered head at the end of the optical fiber, and then emits out from the polymer jacket, and finally irradiates on the tumor which has been injected a photosensitive drug, so that the photosensitive drug (such as PHOTOFRINR) in the tumor produces singlet oxygen by the photochemical reaction, to cause necrosis and apoptosis of the tumor. Thereby the purpose of treating tumors can be achieved.

The present disclosure has high light-emitting efficiency, good the light-emitting effect, and high treatment efficiency.

Example 6

In order to further study the practical effect of the optical fiber puncture needle tubing in this disclosure, the applicant has carried out the study from various aspects, such as the type and length of the blood vessels to be passed through, the passing time, the damage to the blood vessel, the strength of the tip, irradiation effect, treatment efficiency and the accuracy, and so on.

Method:

taking the biopsy for liver tumor sampling as an example, through the Seldinger arterial puncture technique, under the guidance of radiography, the optical fiber puncture need tubing enters the hepatic artery through the femoral artery, then enters the hepatic blood vessels through the hepatic artery, and finally enters the tumor blood vessels, under the auxiliary of the vibration motor. Then, irradiation and treatment of tumor which has been added photosensitizer are performed.

The length of the blood vessel passed through: 1.6 m.

The puncture needle tubing of examples 2 and 3 are tested as the experimental groups 1 and 2 respectively.

Comparative Example 1: this comparative example is performed in the same manner as in example 3, except that there is no polymer jacket.

Comparative Example 2: this comparative example is performed in the same manner as in example 2, except that there is no the structure of tapered head; and the diameter of the head portion of the optical fiber is the same as that of other parts.

Comparative Example 3: this comparative example is performed in the same manner as in example 2, except that there is no the structure of spiral casing 4. That is, the tapered head directly connects with the body portion 8.

Comparative Example 4: the body tube of example 2 is changed to a spring.

Comparative Example 5: the spiral casing 4 of example 2 is changed to a spring.

The results of the above examples are summarized in the table below.

| | Time to reach tumor blood vessels/min | output efficiency of the optical fiber | irradiation efficiency of the optical fiber | tip strength when puncturing/ |
|---|---|---|---|---|
| Experimental group. 1 | 4-10 | 95% | 94% | 2.6N |
| Experimental group 2 | 4-10 | 97% | 96% | 2.6N |
| Com. ex. 1 | 20-30 | 77% | 75% | 2.0N |
| Com. ex 2 | 10-20 | 82% | 65% | 1.0N |

-continued

|  | Time to reach tumor blood vessels/min | output efficiency of the optical fiber | irradiation efficiency of the optical fiber | tip strength when puncturing/ |
|---|---|---|---|---|
| Com. ex 3 | 5-15 | 89% | 60% | 2.4N |
| Com. ex 4 | 20-35 | 89% | 90% | 1.8N |
| Com. ex 5 | 5-15 | 89% | 90% | 1.9N |

In the above table, i) the time to reach the tumor blood vessels refers to the time required to move in the blood vessels before reaching the tumor tissue. ii) the output efficiency of the optical fiber refers to the percentage of light actually irradiated to the photosensitizer in the tumor and the light from the head portion theoretically irradiated to the photosensitizer in the tumor. iii) the irradiation efficiency of the optical fiber refers to the effective amount of light irradiated on the photosensitizer in the tumor, which is in positive ratio with the absorption efficiency of the photosensitizer; iv) the tip strength when puncturing refers to the force of the head of the puncture needle when puncturing the inner wall of the tumor blood vessels.

The results of the above experimental and comparative groups are explained as follows:

Experimental group 1: the structure can move in the blood vessels smoothly; and the outputting rate of light, the irradiation efficiency of the optical fiber, the puncture effect and the therapeutic effect are all better.

Experimental group 2: the structure can move in the blood vessels smoothly; and the outputting rate of light, the irradiation efficiency of the optical fiber, the puncture effect and the therapeutic effect are all better.

Comparative Example 1: Because there is neither polymer jacket nor inverted tooth structure, the moving time in the blood vessels is greatly increased. In addition, since the tapered head is exposed, it has certain brittleness. Therefore, it needs to be careful when moving, and thus affects the moving time in the blood vessels. Because the tapered head is exposed, the endovascular environment has a certain influence on it during the transmission process. In addition, some substances that can affect the refractive index and luminance of light may easy adhered to the tapered head during the process of moving, which leads to the light output efficiency of the optical fiber at the target position is low. Due to its low light output efficiency, it greatly affects the irradiation efficiency of the optical fiber. That is, the light irradiated on the photosensitizer is decreased. The force at the tip when puncturing is decreased obviously.

Comparative Example 2: since there is no tapered head, the strength of the taper structure 31 of the polymer jacket is not enough, which affects moving in blood vessels. In addition, the strength of the tip is low, so it is difficult to achieve the purpose of puncturing blood vessel wall. Moreover, since there is no tapered head, the light is not highly directional. Therefore, some of the light cannot be effectively irradiated to the photosensitizer. In addition, the part needed to be irradiated fewer may be actually irradiated by more light, while the part that needs to be mainly irradiated may be actually irradiated by less light. Therefore, the irradiating blindness is relative larger, the radiation efficiency of the optical fiber is low, thereby greatly influencing the efficiency of the treatment.

Comparative Example 3: as there is no metal casing 4 with the spiral structure, the light is only emitted from the tapered head, the irradiation thereof is only spread over a small area, and specifically only can spread over some important parts; there is almost no light that can irradiate other auxiliary parts. Therefore, it greatly affects the irradiation efficiency, and thus greatly affects their treatment efficiency. In addition, it also influences on the strength of the tip and the moving time in a certain degree.

Comparative Example 4: it is difficult to control the strength and direction of spring, which greatly affects the total moving time. Since the strength thereof also cannot be controlled well, the puncturing effect at a certain point is significantly reduced.

Comparative Example 5: if the selected spring is consistent with the spiral casing in the strength, the flexibility and elasticity thereof are different from those of the spiral casing of the present disclosure. In addition, the direction thereof is not easy to control, resulting in the tip shows less strength than the experimental groups on the whole.

Example 7

A rat tumor model was established. Rats having substantially the same tumor size were taken as the experimental object. In the control, only photosensitizer was applied for treatment. In the experimental group, photosensitizer was applied and the method of the present disclosure was used for illumination.

In the experimental group, the puncture needle tubing described in example 3 is used for irradiation laser.

The control groups 1-3 correspond to comparative groups 1-3 in example 6, and the method of laser irradiation thereof is consistent with that of experimental groups.

Method: ten days after treatment, the rats were dissected. And, the coronal incision was made according to the puncture point on the surface of rats. Tumor size was vertically and horizontally measured. Tumor volume=$a^2b\Pi/6$ (a is a short diameter of the tumor, and b is a long diameter of the tumor). The tumor growth inhibition rate=[(average volume of tumor in the control group−average volume of the tumor in the experimental group/average volume of the tumor in the control group)]×100%. The obtained inhibition rate of the tumor growth is shown as below.

|  | experimental group | control group 1 | control group 2 | control group 3 |
|---|---|---|---|---|
| the inhibition rate of the tumor growth | 83.52% | 62.76% | 60.51% | 49.97% |

Therefore, in the treatment of photodynamic tumor, the efficiency of light emission and illumination has a direct impact on the final treatment effect. The treatment effect of the experimental group is significantly higher than that of the control group.

The above description is only a preferred embodiment of the present disclosure, and is not intended to limit the present disclosure. It should be appreciated that various modifications and changes can be made to the present disclosure. Any modifications, equivalents, improvements, etc. made within the spirit and scope of the present disclosure are intended to be included within the scope of the present disclosure.

The invention claimed is:
1. An optical fiber puncture needle tubing, comprising:
an optical fiber, wherein the optical fiber comprises a body portion and a head portion, wherein the head portion comprises a cylindrical head and a tapered head, the tapered head is a tapered tail end having a tapered diameter formed by a taper method; a periphery of the body portion is wrapped with a body tube, the cylindrical head is wrapped with a metal casing, and a periphery of the tapered head is wrapped with a polymer jacket; one end of the metal casing is fixedly connected with the body tube, and another end is fixedly connected with the polymer jacket; and in the polymer jacket, the part thereof corresponding to the tapered tail end is a taper structure exactly wrapped around the tapered tail end and having a tapered diameter; wherein an inverted tooth structure or an inverted kerf structure is provided on an outside of the polymer jacket, so as to have a smaller resistance when advancing, and have a larger resistance when retreating, thereby effectively reducing a thrust required for puncturing, and wherein the inverted tooth structure has a plurality of frustule structures continuously extending through an entirety of the tapered head.

2. The optical fiber puncture needle tubing according to claim 1, wherein the metal casing is tightly wrapped around the periphery of the cylindrical head of the optical fiber, to integrally connect the optical fiber with the metal casing; wherein the metal casing has a spiral structure with spiral kerfs formed on a metal tube by laser cutting, so that it has a certain strength while increasing a certain flexibility; and wherein the body tube is a spiral tube comprising a plurality of spiral coils, and the spiral tube is a spiral structure having spiral kerfs formed by laser cutting.

3. The optical fiber puncture needle tubing according to claim 2, wherein the periphery of the body portion of the optical fiber is coated with a body portion cladding layer for preventing light from being emitted from a side surface of the optical fiber; and refractive indexes of the tapered head of the optical fiber and the polymer jacket are both 1.45 to 1.55, to emit out light; the tapered head has 7° to 25° of a taper angle β.

4. The optical fiber puncture needle tubing according to claim 1, wherein the inverted-tooth structure of the polymer jacket is formed by the plurality of frustule structures with a small frontend diameter and a large rear-end diameter, so as to make the optical fiber puncture needle tubing easier to move forward and not easy to retreat; inverted kerfs of the inverted kerf structure outside the polymer jacket are formed on an outer surface of a metal tube in the shape of wedge by laser cutting, and the inverted kerf is inclined backward, the width of the inverted kerf decreases gradually from an outside to an inside end.

5. The optical fiber puncture needle tubing according to claim 4, wherein in the inverted-tooth structure, a thickness of a front end of one of the frustule structures is 50 to 70 μm, and a thickness of a rear end of the frustule structure is 90 to 110 μm, and a difference in the thickness between the front end and the rear end is 30 to 50 μm.

6. The optical fiber puncture needle tubing according to claim 1, wherein an end of the optical fiber puncture needle left outside the body is connected with a drive device capable of vibrating backwards and forwards, in order to apply a forward force to the optical fiber puncture needle while vibrating.

7. The optical fiber puncture needle tubing according to claim 6, wherein the drive device is a sonic vibration motor, has 10 μm to 500 μm of amplitude of vibration backwards and forwards, and 10 Hz to 1000 Hz of a vibration frequency; the cylindrical head of the optical fiber at spiral kerfs of the metal casing does not provide with a cladding layer, or has a cladding layer with a refractive index slightly smaller than that of the cylindrical head of the optical fiber, so that only a portion of a light can be emitted from the spiral kerfs of the metal casing; and in the tapered head, a diameter at a foremost end of the tapered head is 10 to 50 μm.

8. The optical fiber puncture needle tubing according to claim 6, wherein a length of the head portion is 7 to 10 mm, and a length of the polymer jacket is 2.5 to 4 mm; the length of the metal casing is 4.5 to 6 mm; in the metal casing, a width a of the spiral kerfs is 0.1 to 0.2 mm, a width of a metal sheet for making the spiral structure of the metal casing is 0.2 to 1 mm; and in the body tube, a thickness of the body tube is 0.05 to 0.1 mm, a width a of the spiral kerfs for forming the spiral structure is 0.02 to 0.2 mm, a width of a spiral sheet for making the spiral structure is 0.5 to 3 mm.

9. The optical fiber puncture needle tubing according to claim 6, wherein a length of the body tube is 1 to 2 m; the body tube is formed by a biomedical metal material including one of stainless steel, synthetic fiber, carbon fiber, titanium alloy, gold, or silver; and a body tube casing is provided outside of the body tube, to increase sealing of the guide tube and reduce resistance, and the body tube casing is coated with a hydrophilic coating or a hydrophobic coating.

10. A method of treating a tumor by using an optical fiber puncture needle, the method comprises:
  piercing a head portion of an optical fiber puncture needle tubing into a blood vessel, wherein the optical fiber puncture needle tubing further comprises a body portion, and the head portion further comprises a cylindrical head and a tapered head, the tapered head is a tapered tail end having a tapered diameter formed by a taper method; a periphery of the body portion is wrapped with a body tube, the cylindrical head is wrapped with a metal casing, and a periphery of the tapered head is wrapped with a polymer jacket; a first end of the metal casing is fixedly connected with the body tube, and a second end is fixedly connected with the polymer jacket, and
  in the polymer jacket, the part thereof corresponding to the tapered tail end is a taper structure exactly wrapped around the tapered tail end and having a tapered diameter; wherein an inverted tooth structure or an inverted kerf structure is provided on an outside of the polymer jacket, so as to have a smaller resistance when advancing, and have a larger resistance when retreating, thereby effectively reducing a thrust required for puncturing, and the inverted tooth structure has a plurality of frustule structures continuously extending through an entirety of the tapered head;
  transmitting the head portion of the optical fiber puncture needle tubing in the blood vessel, wherein an end portion of the optical fiber puncture needle tubing is left outside the blood vessel;
  connecting the end portion of the optical fiber puncture needle tubing with a vibration motor to assist a puncture needle reaching a predetermined site through the blood vessel;
  connecting the optical fiber puncture needle tubing with a laser; and
  transmitting light through the optical fiber to irradiate the tumor.

* * * * *